United States Patent [19]

Atlas et al.

[11] Patent Number: 5,049,499
[45] Date of Patent: Sep. 17, 1991

[54] PROCESS FOR BIOTECHNOLOGICAL UPGRADING OF SHALE OIL

[76] Inventors: Ronald M. Atlas, 1603 Dunbarton Wynde, Louisville, Ky. 40205; Jackie Aislabie, 13 Clouston Cres, Rotorua, New Zealand

[21] Appl. No.: 298,355

[22] Filed: Jan. 19, 1989

[51] Int. Cl.[5] .................. C12R 1/385; C12R 1/39; C12P 1/04; C10G 32/00

[52] U.S. Cl. .................. 435/170; 435/166; 435/167; 435/281; 435/875; 435/876

[58] Field of Search ............... 435/166, 167, 170, 281, 435/875, 876

[56] References Cited

U.S. PATENT DOCUMENTS

| | | | |
|---|---|---|---|
| 3,826,308 | 7/1974 | Compere-Whitney | 435/166 |
| 4,511,657 | 8/1985 | Colarutolo et al. | 435/245 |
| 4,640,767 | 11/1987 | Zajic et al. | 435/281 |
| 4,814,272 | 3/1989 | Wagner et al. | 435/74 |

OTHER PUBLICATIONS

CA111:81053c Aug. 28, 1989, vol. 111, No. 9, Aislabie et al. "Appl. Biochem Biotech 1988, Pub. 1989", 20-21, 799-807.
CA84:182303r, Jun. 28, 1976, vol. 84, No. 26, Westlake et al., "Canadian J. Microbiol." 1976 22(2)221-227.
CA109:208028s, Dec. 5, 1988, vol. 109, No. 23, Aislabie et al., "Appl. Environ Microbiol" 1988 54(9)2197-2202.

*Primary Examiner*—Herbert J. Lilling

[57] ABSTRACT

A process for biotechnological upgrading of shale oil in selectively removing damaging nitrogen-containing compounds comprising treating the raw shale oil with special microbial cultures having specific ability to degrade the harmful nitrogen-containing compounds, such as the amines, nitriles and heterocyclics as the quinolines and pyridines, and converting them into non-damaging components.

11 Claims, 5 Drawing Sheets

PROCESS FOR BIOTECHNOLOGICAL UPGRADING OF SHALE OIL

BACKGROUND OF THE INVENTION

A deposit of the material set out herein has been deposited in American Type Culture Collection No. ATCC 55084, 55083, 55081.

1. Field of the Invention

This invention relates to a new process for biotechnological upgrading of raw shale oil. More particularly, the invention relates to a new biotechnological process for treating raw shale oil to remove the nitrogen-containing contaminants thereof.

Specifically, the invention provides a new technique using microbial cultures to selectively remove damaging nitrogen-containing compounds, such as, for example, the aliphatic and heterocyclic nitrogen compounds as nitriles, quinolines and the like, from raw shale oil without attacking the valuable hydrocarbons in the said oil. The new process broadly comprises treating the raw shale oil with special microbial cultures having specific ability to degrade the harmful nitrogen-containing compounds, such as the amines, nitriles and heterocylics as the quinolines and pyridines, and converting them into non damaging components, without degrading any of the valuable hydrocarbons contained in said oil, said treatment being accomplished in the presence of an alternative source of carbon, such as glucose or succinate under aerobic conditions.

The invention further provides a technique for the preparation of microbal populations which are specific to the degradation of the aliphatic and heterocyclic nitrogen-containing compounds generally found in the raw shale oil.

2. Prior Art

World wide demand for hydrocarbons and related products is continuing at a high annual rate. Crude petroleum and natural gas are basic in satisfying these demands but shortages can be forseen in the near future even though new oil and gas resources are being discovered. Therefore, alternate sources and feed stocks, such as coal, tar sands, oil shale and solid crudes are receiving greater consideration.

Oil shales found in large quantities in various locations throughout the world are an ideal source for obtaining additional quantities of hydrocarbons and related products. Oil shales consists of compacted sedimentary inorganic rock particles, generally laminated and partly or entirely encased with a high molecular weight organic solid material called kerogen, which is generally present in amounts of about 6 to 30 percent by weight of the shale. Kerogen is derived from aquatic organisms or waxy spores and pollen grains, comprising hydrocarbons and complex organic-nitrogen, oxygen and sulfur compounds.

Oils produced from the crude oil shales are unlike oil from petroleum reservoirs in having much higher concentrations of the nitrogen and sulfur compounds. The nitrogen content, for example, varies from about 0.5 to 2% which is much higher than the amount in crude oil (about 0.094%).

Because of the excessive amounts of nitrogen and sulfur compounds in the oils obtained by retorting of shales, such oils are unsuited for direct refining into useful fuels. It has been found, for example, that the nitrogen-containing compounds act as poison for the refining catalysts and together with the oxygen compounds cause poor stability of the shale oils.

Attempts have been made in the past to upgrade the shale oils by using modified refinery techniques, particularly by thermal means using molecular hydrogen. High intensity hydrotreatments are very costly and low intensity hydrotreatments have not been entirely satisfactory as they have generally resulted in a low conversion to the desired higher molecular weight products and the desired liquid products have been of low quality in that they may still contain considerable amounts of nitrogen, sulfur and oxygen contaminates.

Although efforts have been made to treat refined oils produced from petroleum to reduce the relatively low concentrations of nitrogen-containing compounds microorganisms and biotechnological processes have not been previously reported for removal of nitrogen from shale oils. Also, previous reports of microbial attack of nitrogen-containing compounds in fuels have not demonstrated selective removal so that hydrocarbons were also degraded. For example, U.S. Pat. No. 3,069,325, which discloses a method for treatment of jet fuels with strains of microorganisms obtained from sea water in the absence of nutrients reported reduction of the nitrogen content from 0.02 to 0.002% relied upon hydrocarbon degrading microorganisms. This process reduced the value of the fuel by removing the valuable hydrocarbons.

It is an object of the invention, therefore, to provide a new process for the treatment of raw shale oil itself to effect a degradation of the damaging nitrogen-containing components. It is a further object to provide a new process for the treatment of raw shale oil to remove the nitrogen-containing contaminants without degrading the important hydrocarbon components. It is a further object to provide a biotechnological method for treating raw shale oil to remove contaminating materials. It is a further object to provide a new process for treating raw shale oil to remove the aliphatic nitrogen-containing compounds, such as the aliphatic amines and nitriles. It is a further object to provide a process for treating raw shale oil to remove the heterocyclic nitrogen compounds such as the quinolines, pyridines and the like. These and other objects will be apparent from the following detailed description thereof.

SUMMARY OF THE INVENTION

It has now been discovered that these and other objects can be accomplished by the new process of the present invention which provides for the first time an effective method for treatment of raw oil shale to degrade the damaging nitrogen-containing compounds.

The new process broadly comprises treating the raw shale oil with special microbial cultures having specific ability to degrade the harmful nitrogen-containing compounds and convert them into non-damaging components, without degrading any of the valuable hydrocarbons contained in the shale oil, said treatment being accomplished in the presence of an alternative source of carbon, such as, for example, glucose or succinate and preferably under aerobic conditions.

It has been found that by the use of the above-noted process one is able to reduce and in many cases completely eliminate the unwanted nitrogen compounds from the raw shale oil. It has been found, for example, that by the use of the process of the invention one can completely utilize or degrade the homologous series of nitriles, and particularly the lower members of the series, which make up about 10% of the nitrogen-containing compounds in the raw shale oil. In addition, the aliphatic amines, which make up about 40% of the nitrogen-containing compounds appear also to be removed.

Further advantage is also found in the fact that by the use of the specially prepared microbial populations, and special mixtures thereof, one is able to degrade the most difficult heterocyclic nitrogen-containing compounds, such as the quinolines, isoquinolines, pyridines, pyrroles, and carbazoles.

Surprisingly, such biodegradation of the nitrogen-containing compounds is accomplished without any lost of the valuable hydrocarbon components present in the shale oil.

DESCRIPTION OF THE DRAWINGS

The various objects and features of the present invention will be more fully understood by reference to the accompanying drawings.

With reference to FIGS. 1-A, 1-B, 1-C and 1-D tracing 1-A shows the fraction recovered from a sterile control after 14 days of incubation, 1-B shows the results with the enrichment culture after 3 days, 1-C shows the results with the enrichment culture after 7 days, and 1-D shows the results with the enrichment culture after 14 days. The profile of the nitriles in the sterile control after this incubation period is identical with that for the initial oil, indicating no abiotic degradation of these nitriles. The internal standard is quinoline (Q). The chain lengths of the n-nitriles are indicated. The unsaturated nitriles occur just preceding the n-nitriles of corresponding chain lengths.

With reference to FIGS. 2-A, 2-B and 2-C the profiles for each of the fractions are identical with those for the sterile control and the initial oil, indicating no abiotic losses or biodegradation of the compounds in these fractions. In chromatogram 2-A, the internal standard is 7,8-benzoquinoline (BQ); quinoline (Q) and isoquinoline (IQ) are identified and the ranges of $C_1$-$C_4$ derivatives of quinoline and isoquinoline are shown. In chromatogram 2-B, the internal standard is HMB; the series of n-alkanes is shown; the n-alkanes are proceded by a series of 1-alkenes. In chromatogram 2-C the internal standard is HMB. Labelled peaks are 1-methylnaphthalene (1-MN), 2-methylnaphthalene (2-MN), fluorene (F), and phenanthrene (P).

With reference to FIGS. 3-A and 3-B, A=uninoculated control, B=after 14 d incubation with a nitrogen heterocycle degrading enrichment culture. The peaks removed due to biodegradation are indicated by the arrows. The compounds in the fraction are A=quinoline, B=isoquinoline, C=2-methylquinoline, D=8-methylquinoline, E=1-methylisoquinoline, F=6-methylquinoline/7-methylquinoline (these compounds coelute), G=unidentified, H=unidentified and BQ=7,8-benzoquinoline internal standard.

With reference to FIG. 4, the fraction contains the same compounds as labelled in FIG. 3. The peaks removed due to biodegradation are indicated by the arrows. The compounds removed in the fraction are A=quinoline, B=isoquinoline, D=8-methylquinoline, F=6-methylquinoline/7-methylquinoline, G=unidentified, H=unidentified, J=unidentified, L=unidentified, BQ=7,8-benzoquinoline internal standard.

With reference to FIG. 5, the fraction contains the same compounds labelled in FIG. 3. The peaks removed due to biodegradation are indicated by the arrows. A=quinoline, D=8-methylquinoline, F=6-methylquinoline/7-methylquinoline, G=unidentified, H=unidentified, BQ=7,8-benzoquinoline internal standard.

DETAILED DESCRIPTION OF THE INVENTION

Figure 1A:
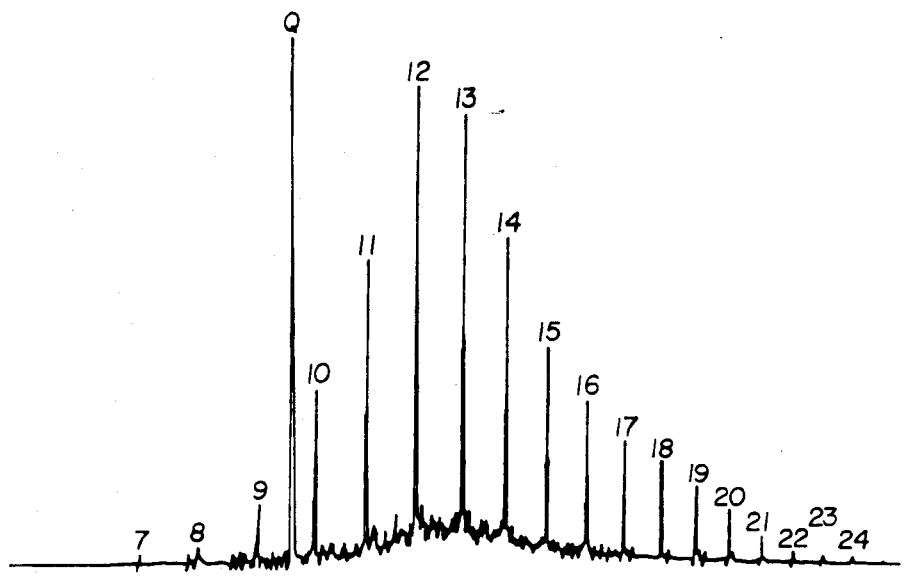
FIGS. 1-A, 1-B, 1-C and 1-D are gas chromatographic tracings of nitrile fractions recovered from a sterile control after up to 14 days of incubation with an enriched culture.
Figure 1B:
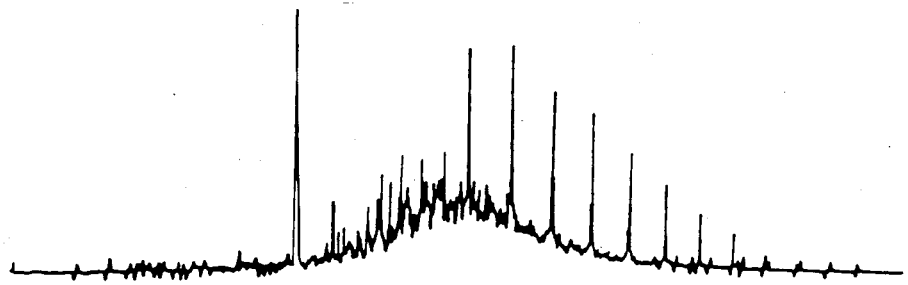
Figure 1C:
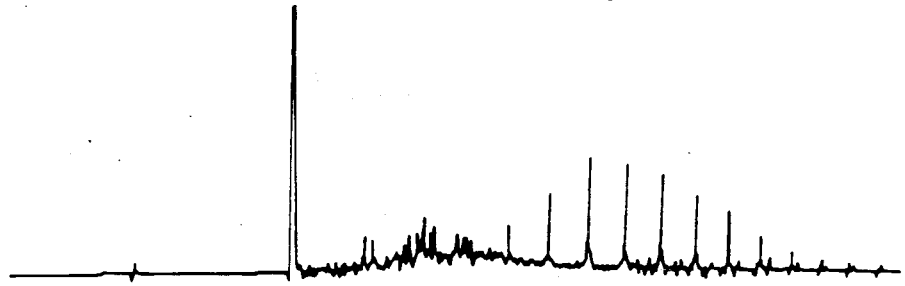
Figure 1D:

While the above-described description of the invention and the attached drawings have been made in rather specific terms, it should be understood that various changes can be made in procedure and components and use without departing from the scope of the present invention.

Any raw oil shale containing kerogen can be used in the process of the invention. Oil shales of the Eocene period generally found in the western United States and particularly the Northwestern area of Colorado and in the adjoining areas of Utah and Wyoming are suitable for use in this invention. These oil shales have an organic carbon to hydrogen weight ratio typically of less than 8:1 and usually of 7:1 to 8:1, and Fisher Assays in the order of 25 gallons per ton of ore. Oil shales having large quantities of "Black Shale" from deposits such as Devonian and Missippian, generally found in the eastern portion of the United States are especially suited for use in the process of the present invention. These oil shales have been found to have organic carbon to hydrogen weight ratios typically in the order of 8:1 to about 10:, and Fisher Assays of less than 15 gallons of oil per ton of ore.

The process of the invention is also particularly useful for other shales found throughout the world, and especially those found in Australia. The shale oil used in many of the experiments reported herein was the middle cut of a raw shale oil (250° to 400° C. boiling range) produced at the Taciuk Processor Pilot Plant by pyrolysis of shale from the Stuart Deposit, Queensland, Australia. This shale oil contains 0.87% Kjeldahl nitrogen analysis, with the nitrogen found in aliphatic amines, nitriles, and heterocyclic nitrogen compounds, such as quinolines, isoquinolines, pyridines, pyrroles and carbazoles. Approximately half of the nitrogen is contained in the heterocyclic compounds and the remainder occurs primarily as aliphatic nitriles and amines.

The microbial cultures used in the process of the invention are those specific towards the degradation of the harmful nitrogen-containing compounds, such as the above-noted amines, nitriles and heterocyclic nitrogen-containing compounds found in the raw oil shale. These cultures are preferably obtained by a technique involving the production of a series of enrichment cultures wherein microbial cultures present in soil sources contaminated with petroleum were repeatedly added to media containing the shale oil as the only source of nitrogen. After a series of subcultures to ensure maintenance of growth on medium in which the shale oil was the sole source of nitrogen, the enriched cultures are analyzed to determine which compounds if any, in the shale oil have been changed. Sterile controls are included to distinguish nonbiological changes in the oil from those due to biodegradation.

As shown in the Examples at the end of the specification, by using this technique with a series of subcultures, microbial populations were developed which were specific to the degradation of the nitriles, amines, as well as the heterocyclic nitrogen-containing compounds, such as the quinolines and isoquinolines.

An example of strains found to be specific to the degradation of nitriles were a *Pseudomonas fluorescens* strain and strains of Alcaligenas.

A strain found to be specific to the degradation of the heterocyclic nitrogen-containing compounds was *Pseudomonas aeruginosa*. A mixed culture of unidentified bacteria also demonstrated selective degradation of heterocyclic nitrogen-containing compounds including isoquinolines. The degradation of many of these compounds involved formation of hydroxylated heterocyclic nitrogen-containing compounds that were soluble in water and could be removed from the oil by water extraction.

By using a mixture of such enriched cultures obtained for specific nitrogen-containing compounds, one is able to remove from the raw shale oil most or all of the damaging nitrogen-containing compounds.

A variety of nutrient media can be used in preparation of the enrichment cultures. Preferred components include the sulfates, phosphates, chlorides, etc. such as, for example, $MgSO_4$, $CaCl_2$, $KHPO_4$ and $FeCl_3$, and the like, and suitable mixtures thereof.

In effecting the process of the present invention, a sterile medium is prepared containing the raw shale oil and an alternative source of carbon and then the medium is inoculated with the desired microbial strain or strains to effect the degradation. The amount of the raw shale oil included in the medium may vary over a wide range. In general, the raw shale oil will vary up to 1% (wt/vol).

The nature of the alternative source of carbon to be added to the reaction mixture may vary over a wide range, and includes many of the oil soluble organic compounds high in carbon, such as the sugars, esters and the like. Glucose and succinate are particularly preferred. The amount of the alternative source of carbon to be included in the medium may vary greatly, but should be kept as low as possible to still support microbial activity, e.g. 1% or less.

The temperature employed in the above process may vary over a considerable range. In most cases, the temperature will vary from about 20° C. to about 40° C., and preferably about 25° C. to 30° C. However, higher or lower temperatures can be employed as needed.

Since the process proceeds slowly under anaerobic conditions, it is preferred to conduct the process under aerobic conditions.

The reaction medium is preferably stirred or shaken to speed the reaction. As shown in the examples, the reaction medium is preferably placed in a rotary shaker at speeds of about 200 rpm.

The length of the reaction may also vary depending upon the specific ingredients, temperature, etc. In most cases, the desired degradation of the nitrogen-containing compounds can be accomplished in a matter of hours or days, such as from 0.5 to 14 days.

The nitrogen-containing compounds consumed in the reaction may be metabolized by the microbial population and thus appear as proteins in their composition, or they may be degraded into water soluble products which may be easily removed by washing the resulting oil fraction.

At the conclusion of the reaction, the media can be extracted with suitable solvent, such as methylene chloride at neutral pH and the oil concentrated by suitable means, such as a rotary evaporator, distillation column and the like.

The oil obtained by the above-noted process of the invention will be mostly free or entirely free of the nitrogen compounds but will still retain the desired aliphatic and aromatic hydrocarbons in substantially the same amount as in the original raw shale oil. This selective removal capacity is critical for upgrading of shale oil or other synthetic fuels because of the need to retain the caloric value of the hydrocarbons within the fuel. The oil so obtained can be further extracted, distilled or stripped to produce a variety of fractions, such as jet fuels, gasoline, etc, as needed.

To illustrate the process of the invention, the following examples are given. It should be understood, however, that these examples are given only as an illustration and should not be regarded as limiting the invention in any way. Unless otherwise indicated, parts are parts by volume.

EXAMPLE I

This example illustrates the use of the process of the invention in treatment of raw shale oil to remove nitrile contaminates.

An enriched culture containing microbial strains specific towards nitriles was prepared as follows: Several soil sources contaminated with petroleum, including soils from oily sludge landfarming drill cores, were used as source of inocula for the enriched cultures. Culture conditions were established to enrich for microbial populations capable of using the nitrile compounds in the shale oil. Ten grams of each soil were added to 100 ml of a nitrogen-free medium containing (in grams per liter), $MgSO_4$, 0.2; $CaCl_2$, 0.02; $KH_2PO_4$ 1; $K_2HPO_4$ 1; $FeCl_3$, 0.05. The pH was adjusted to 7.5, and the medium was then autoclaved. After sterilization the medium was amended with a sterile glucose solution to give a final concentration of 0.1% (wt/vol) and the shale oil to give a concentration of 1% (wt/vol). The shale oil was thus the sole source of nitrogen but not the sole source of carbon for these enrichments. The shale oil used in these enrichment cultures was the middle cut of a raw shale oil (250° to 400° C. boiling range) produced at the Taciuk Processor Pilot plant by pyrolysis of shale from the Stuart Deposit, Queensland, Australia. This shale oil contains 0.87% Kjeldahl nitrogen with the nitrogen found in aliphatic amines (40%), nitriles (10%), and the heterocyclic nitrogen compounds (50%) such as quinolines, isoquinolines, pyridines, pyrroles and carbazoles. The enrichments were incubated at 28°

C. on a rotary shaker at 200 rpm. The enrichments have been maintained by monthly transfers into fresh medium.

After at least eight subcultures to ensure maintenance of growth on medium in which the shale oil was the sole source of nitrogen but not carbon, enrichment cultures showing emulsification and visible changes in the oil were analyzed to determine which compounds in the shale oil had been biodegraded. For these analyses, the enrichment cultures were incubated for 28 days at 28° C. on a rotary shaker at 200 rpm in the same medium used for the initial enrichments as noted above, e.g. those containing the glucose solution and the shale oil. Sterile controls were included to distinguish nonbiological changes in the oil due to biodegradation.

The residual oil was recovered by extraction with methylene chloride and analyzed. Prior to extraction, HMB was added to each culture flask as an internal standard. The media were extracted with methylene chloride at neutral pH, and the oil was concentrated by using a rotary evaporator. The oil was fractionated by modification of the column chromatographic method described by Fedorak and Westlake (Appl. Environ. Microbiol. 47:858-862.).

After the solvent volume had been reduced under vacuum, the fractions were analyzed by capillary gas-liquid chromatography. An Ultra-2-coated fused silica column (25 cm by 0.2 mm; Hewlett Packard) was used for compound separation. The saturate and aromatic fractions were analyzed with a Hewlett Packard model 5840 gas chromatography with a flame ionization detector. the nitrile and heterocyclic nitrogen fractions were analyzed with a nitrogen-specific detector.

RESULTS

The GC analyses of the oil fractions recovered from the broth enrichment cultures in which the shale oil was the sole nitrogen source and glucose was an alternative carbon source showed selective microbial attack on the aliphatic nitrile compounds from the shale oil. The same preferential attack on the nitrile fraction was observed when succinate was used instead of glucose as the alternative carbon source.

Figure 2A:
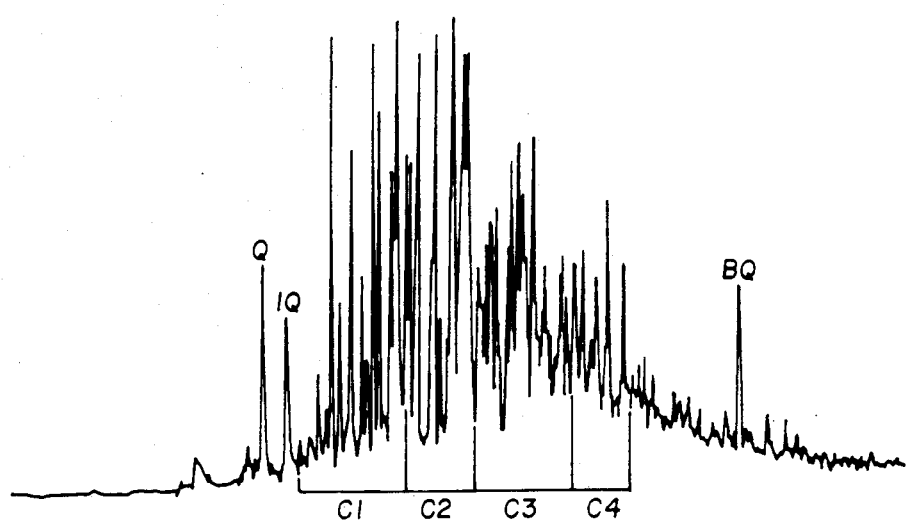
FIGS. 2-A, 2-B and 2-C are gas chromatographic tracings of heterocyclic nitrogen (A), aliphatic hydrocarbon (B), and aromatic hydrocarbon (C) fractions recovered after 28 days incubation from an enrichment culture.
Figure 2B:
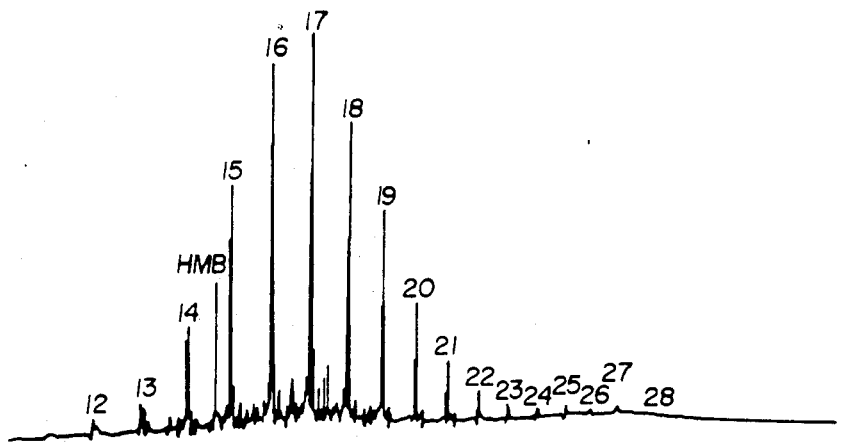
Figure 2C:
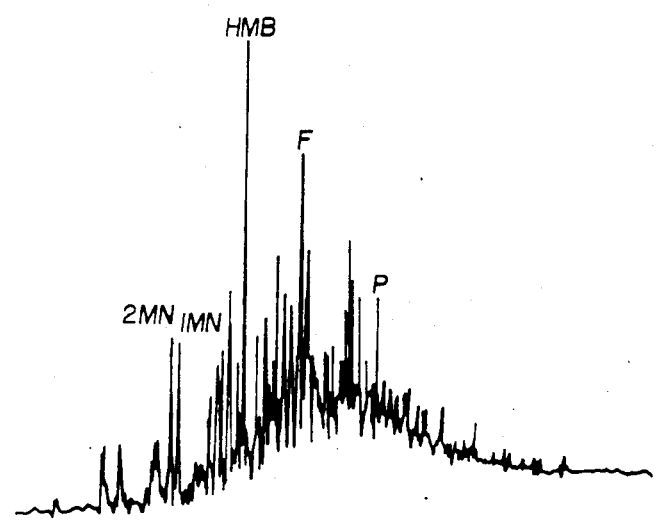

The GC tracings of nitrile fractions recovered after 14 days of incubations are shown in FIG. 1. A shows the fraction recovered from a sterile control after 14 days of incubation, B shows the results with the enrichment culture after 3 days, C shows the results after 7 days and D shows the results after 14 days. The profile of the nitriles in the sterile control after this incubation period is identical with that for the initial oil, indicating no abiotic degradation of these nitriles. The internal standard is quinoline (Q). The chain length of the n-nitriles indicated. The process was continued for a period of 28 days with the results shown in FIG. 2 demonstrating that no attack on the hydrocarbon (aliphatic and aromatic) or nitrogen heterocycle fraction occurred during 28 days incubation.

EXAMPLE II

A *P. fluorescens* strain was isolated from the enrichment culture shown in Example I above and inoculated into the same medium used initially for enrichment culture with 1% raw shale oil as the sole source of nitrogen and 0.1% glucose as an alternative carbon source, with a resulting preferential removal of the lower-molecular weight nitriles. During 7 days of incubation the organism degraded unsaturated nitriles in the range from $C_7$ to $C_{12}$. there was no removal of unsaturated nitriles above $C_{13}$ or saturated nitriles above $C_{12}$ from the shale oil by this particular bacterial strain. There was no change in the aliphatic or aromatic hydrocarbons when this strain was utilized. However, when the shale oil was used as the sole source of carbon, aliphatic hydrocarbons were degraded in addition to the nitriles.

EXAMPLE III

A pure culture of *Pseudomonas aeruginosa* SPI was also inoculated into the same medium used initially for enrichment culture with 1% raw shale oil as the sole source of nitrogen and 0.1% glucose as the alternative carbon source. The same results as shown in Example I were obtained. This strain is able to degrade high and low molecular weight nitriles.

EXAMPLE IV

This example illustrates the use of the process of the invention in treatment of raw shale oil to remove heterocyclic nitrogen-containing compounds, such as quinolines and pyridines.

Figure 3A:
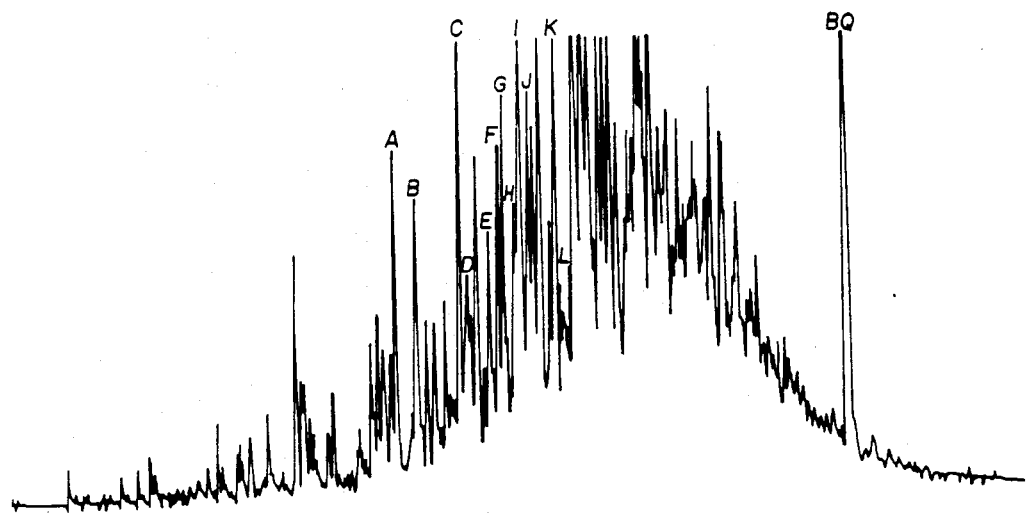
FIG. 3 is a capillary gas chromatographic analysis of the heterocyclic nitrogen fraction of Stuart shale oil using a nitrogen specific detector, A is the uninoculated control and B is after 14 days incubation with a nitrogen-heterocyclic-degrading enrichment culture.
Figure 3B:
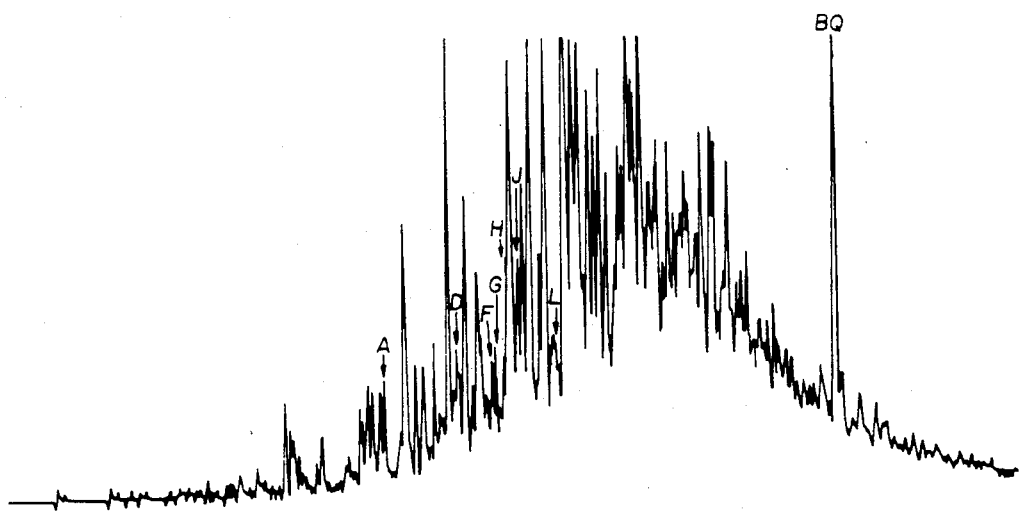

A shale oil-utilizing enrichment culture was initially established by inoculating oil contaminated soil into a nitrogen free phosphate salts medium containing 1% raw shale oil=supplemented with 0.1% pyridine, as the sole source of nitrogen and 0.1% succinate as an alternate carbon source. To specifically enrich for organisms that could degrade heterocyclic nitrogen compounds. a subculture was inoculated into phosphate salts broth with 0.1% succinate and 1% heterocyclic compounds fraction previously extracted from the raw shale oil. Gas chromatographic-mass spectral analyses showed that the extracted heterocyclic nitrogen compounds were primarily quinolines and isoquinolines (FIG. 3.)

A subculture from this enrichment was made into a medium containing 0.015% quinoline as the sole source of carbon and 0.1% ammonium sulfate as an alternate source of nitrogen. A quinoline-degrading strain of *P. aeruginosa* was subsequently isolated from this subculture and maintained in phosphate salts broth containing 0.015% quinoline as the sole source of carbon and nitrogen.

Figure 5:
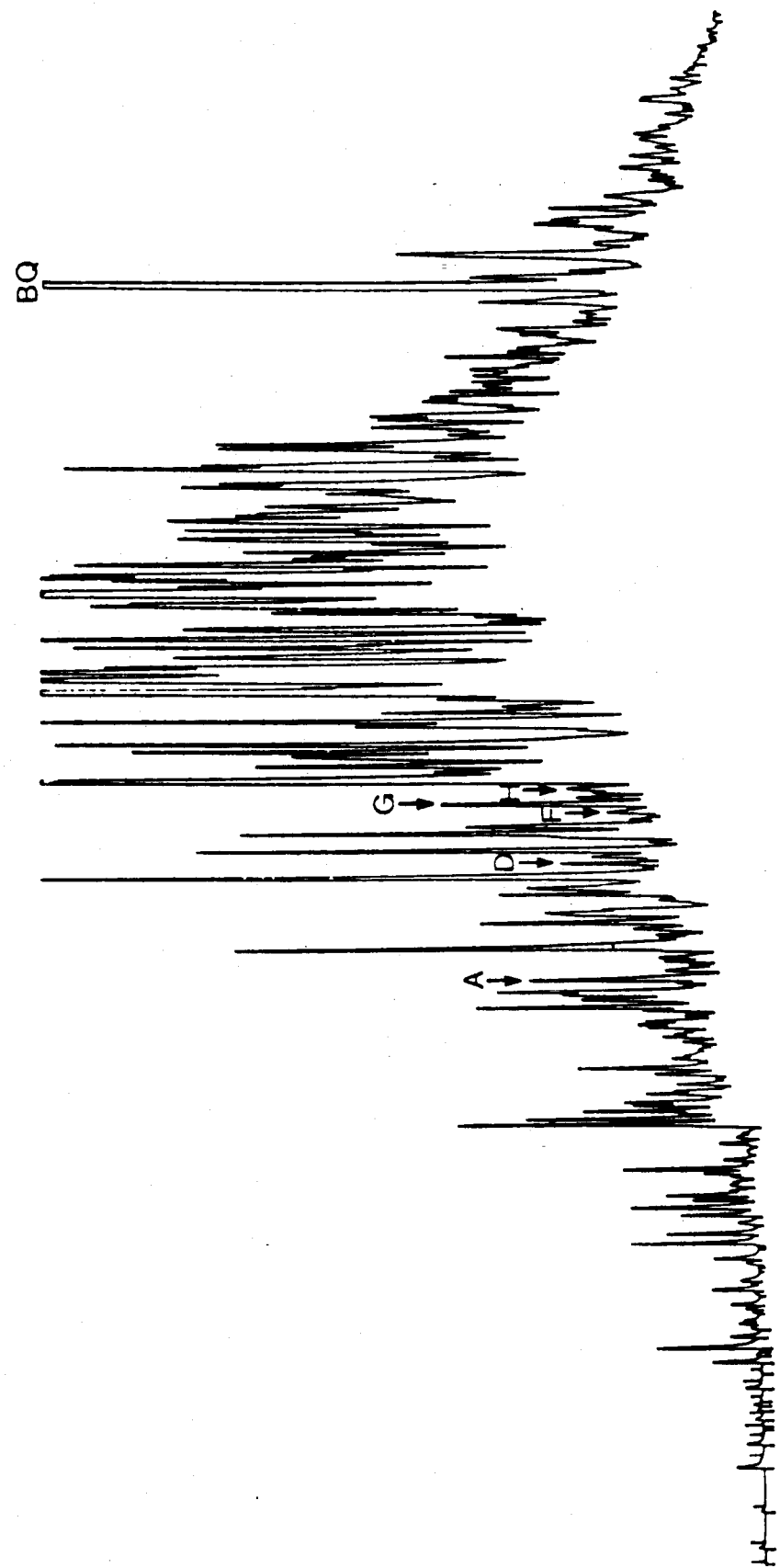
FIG. 5 is a capillary gas chromatographic analysis of Stuart raw shale oil after 7 days incubation with a quinoline-degrading strain of Pseudomonas aeruginosa using a nitrogen specific detector.

This quinoline-degrading strain of *P. aeruginosa* was inoculated into phosphate salts broth containing 1% raw shale oil and 0,1% succinate as an alternate carbon source. Cultures were incubated for 7 days at 28° C. with shaking at 200 rpm and the residual heterocyclic nitrogen compounds were then extracted and analyzed with the results as shown in FIG. 5.

EXAMPLE V

A subculture of the shale oil-utilizing enrichment culture disclosed in Example IV was prepared in a phosphate salt broth containing 0.1% pyridine as sole source of carbon and 0.1% ammonium sulfateas alternate nitrogen source and subsequently into phosphate salts both with 0.1% pyridine as sole source of carbon and nitrogen. A pyridine-degrading Pseudomanas species was isolated from this culture.

EXAMPLE VI

Figure 4:
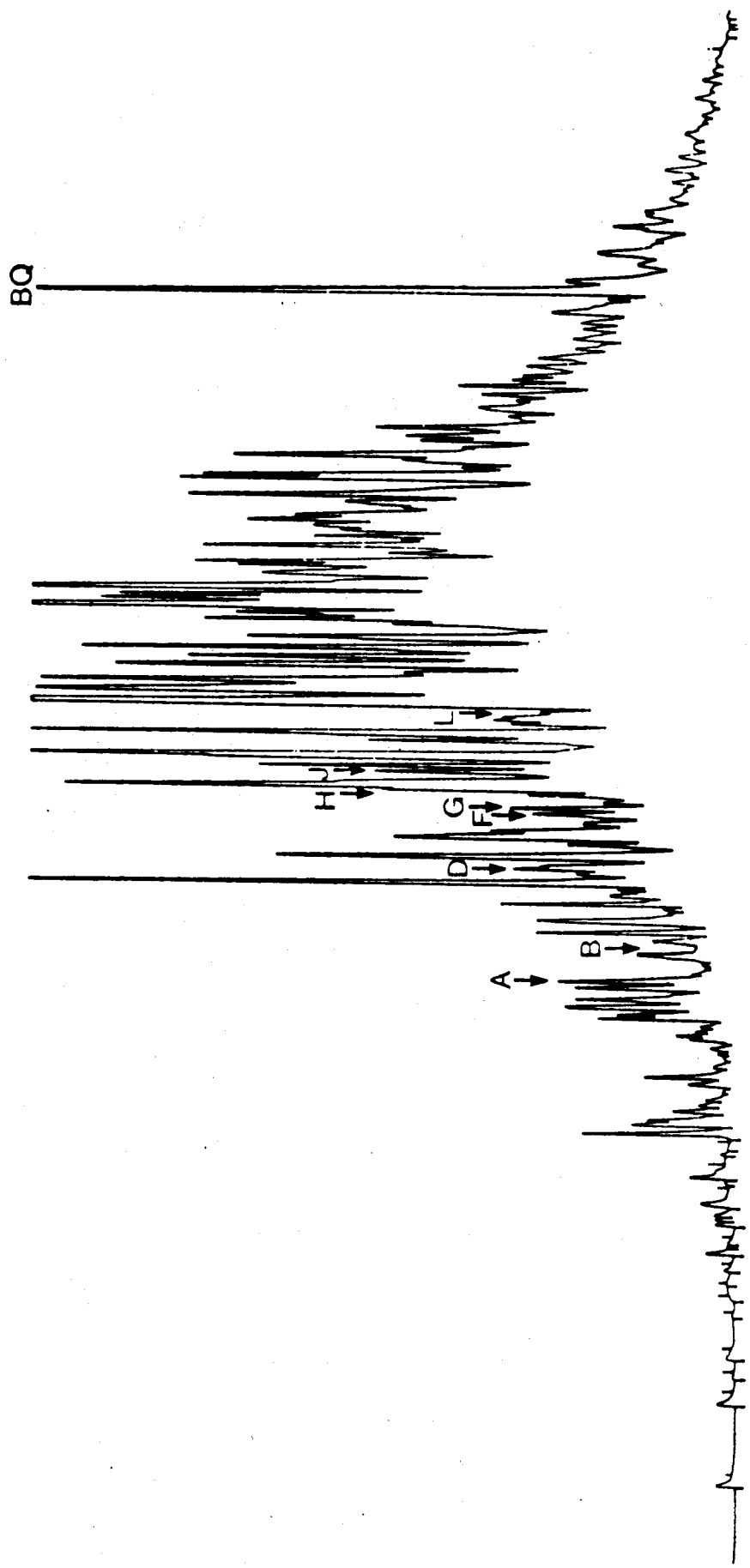
FIG. 4 is a capillary gas chromatographic analysis of the heterocyclic nitrogen fraction of Stuart shale oil using a nitrogen detector after incubation with a mixture of a nitrogen-heterocycle-degrading enrichment culture and an isoquinoline-degrading enrichment culture.

An isoquinoline-degrading enrichment culture was established by inoculating oil contaminated soil into a phosphate salt broth containing 0.015% emulsified isoquinoline as the carbon source and 0.1% ammonium sulfate as an alternate nitrogen source. This isoquinoline-degrading culture and the original heterocyclic nitrogen-degrading enrichment culture were added together to phosphate salts broth containing 1% heterocyclic nitrogen as the sole source of carbon and 0.1% ammonium sulfate as an alterate nitrogen source. After one month incubation at 28° C. with shaking at 100 rpm, the residual heterocyclic compounds were extracted and analyzed by capillar gas chromatography with the results as shown in FIG. 4.

The conventional expression "succinate" as used herein refers to sodium succinate.

We claim as our invention:

1. A process for biotechnological upgrading of raw shale which is free of damaging nitrogen-containing compounds, said oil containing nitrogen-containing compounds along with the hydrocarbons which comprises inoculating the raw shale oil with microbial cultures selected from the group consisting of *Pseudomonas aeruginosa* ATTC 55081, *Pseudomonas aeruginosa* ATTC 55083, *Pseudomonas fluorescens* 55084 and mixtures thereof, which possess the capability of selectively degrading the nitrogen-containing compounds without attacking the hydrocarbons contained therein, said treatment being conducted in the presence of a source of carbon other than that contained in the raw shale.

2. A process as in claim 1 wherein the microbial culture is one which possesses the capability of selectively degrading the aliphatic nitrogen-containing compounds in the oil.

3. A process as in claim 1 wherein the microbial culture is one which possesses the capability of selectively degrading the heterocyclic nitrogen-containing compounds contained in the raw shale oil.

4. A process as in claim 1 wherein the microbial culture is one which possesses the capability of selectively degrading the aliphatic nitriles contained in the raw shale oil.

5. A process as in claim 1 wherein the microbial culture is one which possesses the capability of degrading the aliphatic amines in the raw shale oil.

6. A process as in claim 1 wherein the microbial culture is one which possesses the capability of selectively degrading the quinolines contained in the shale oil.

7. A process as in claim 1 wherein the microbial culture is one which possesses the capability of selectively degrading the isoquinolines contained in the raw shale oil.

8. A process as in claim 1 which is conducted in the presence of an alternate source of carbon comprising an oil soluble organic compound high in carbon.

9. A process as in claim 1 wherein the process is conducted in the presence of glucose as the alternate source of carbon.

10. A process as in claim 1 wherein the process is conducted in the presence of sodium succinate.

11. A process as in claim 1 which is conducted under aerobic conditions.

* * * * *

UNITED STATES PATENT AND TRADEMARK OFFICE
CERTIFICATE OF CORRECTION

PATENT NO. : 5,049,499

DATED : Sep. 17, 1991

INVENTOR(S) : Ronald M. Atlas, et al.

It is certified that error appears in the above-identified patent and that said Letters Patent is hereby corrected as shown below:

On the title page, insert the following:

--Southern Pacific Petroleum, Ogden, UT--.

Signed and Sealed this

Twenty-third Day of February, 1993

Attest:

STEPHEN G. KUNIN

Attesting Officer

Acting Commissioner of Patents and Trademarks